US009101570B1

(12) United States Patent
Duffy, Jr. et al.

(10) Patent No.: US 9,101,570 B1
(45) Date of Patent: Aug. 11, 2015

(54) ADULT AND NEONATAL STEM CELL THERAPY TO TREAT DIABETES THROUGH THE REPAIR OF THE GASTROINTESTINAL TRACT

(75) Inventors: Neil F. Duffy, Jr., Brighton, MA (US); Andrew McGillicuddy, Hanover, MA (US)

(73) Assignee: EndoCellutions, Inc., Marshfield, MA (US)

( * ) Notice: Subject to any disclaimer, the term of this patent is extended or adjusted under 35 U.S.C. 154(b) by 65 days.

(21) Appl. No.: 12/697,537

(22) Filed: Feb. 1, 2010

Related U.S. Application Data

(60) Provisional application No. 61/152,417, filed on Feb. 13, 2009.

(51) Int. Cl.
| | |
|---|---|
| *A61K 35/12* | (2015.01) |
| *A61K 35/28* | (2015.01) |
| *C12N 5/07* | (2010.01) |
| *A61K 35/50* | (2015.01) |
| *A61K 35/35* | (2015.01) |
| *C12N 5/077* | (2010.01) |
| *C12N 5/0775* | (2010.01) |
| *C12N 5/074* | (2010.01) |

(52) U.S. Cl.
CPC ............ *A61K 35/12* (2013.01); *A61K 35/28* (2013.01); *A61K 35/35* (2013.01); *A61K 35/50* (2013.01); *C12N 5/06* (2013.01); *C12N 5/0607* (2013.01); *C12N 5/0653* (2013.01); *C12N 5/0663* (2013.01); *C12N 5/0667* (2013.01); *Y10S 514/866* (2013.01)

(58) Field of Classification Search
CPC ....... A61K 35/12; A61K 35/35; A61K 35/28; A61K 35/50; C12N 5/06; C12N 5/0607; C12N 5/0653; C12N 5/0663; C12N 5/0667; C12N 5/0675; Y10S 514/866
See application file for complete search history.

(56) References Cited

U.S. PATENT DOCUMENTS

| | | | |
|---|---|---|---|
| 5,175,103 A | 12/1992 | Lee et al. | |
| 5,753,491 A | 5/1998 | Major et al. | |
| 5,753,505 A | 5/1998 | Luskin | |
| 5,851,832 A | 12/1998 | Weiss et al. | |
| 5,869,463 A | 2/1999 | Major et al. | |
| 5,968,829 A | 10/1999 | Carpenter | |
| 5,980,885 A | 11/1999 | Weiss et al. | |
| 5,981,165 A | 11/1999 | Weiss et al. | |
| 6,025,157 A | 2/2000 | Klein et al. | |
| 6,497,872 B1 | 12/2002 | Weiss et al. | |
| 6,808,702 B2 * | 10/2004 | Pasricha et al. | 424/93.1 |
| 7,122,058 B2 | 10/2006 | Levine et al. | |
| 2002/0025308 A1* | 2/2002 | Costantino et al. | 424/93.21 |
| 2006/0051865 A1* | 3/2006 | Higgins et al. | 435/366 |
| 2008/0260703 A1* | 10/2008 | Riordan et al. | 424/93.7 |

OTHER PUBLICATIONS

Bendayan and Park. Presence of extrapancreatic islets of Langerhans in the duodenal wall of the rat. Diabetologia (1991) 34:604-606.*
Chao et al. Islet-Like Clusters Derived from Mesenchymal Stem Cells in Wharton's Jelly of the Human Umbilical Cord for Transplantation to Control Type 1 Diabetes. PLoS ONE 3(1): e1451 p. 1-9.*
Koblas et al. The Application of Umbilical Cord Blood Cells in the Treatment of Diabetes Mellitus. The Review of Diabetic Studies vol. 2. No. 4. 2005. p. 228-234.*
Caiazzo et al. Evaluation of Alternative Sites for Islet Transplantation in the Minipig:Interest and Limits of the Gastric Submucosa. Transplantation Proceedings, 39, 2620-2623 (2007).*
Greenway SE, et al. "Effects of obesity surgery on non insulin-dependent diabetes mellitus." *Arch Surg.* 2002.137: 1109-1117.
Herman MA and Kahn BB. "Glucose transport and sensing in the maintenance of glucose homeostasis and metabolic harmony." *J Clin Invest.* 2006.116(7): 1767-1775.
Vina R, et al. "Cell therapy: a new challenge for Type 2 Diabetes." Poster presentation at International Society of Cellular Therapy. May 2008. [online, retrieved on Aug. 10, 2012]. Retrieved from the internet URL: http://www.fundacionfernandezvina.org/publicaciones_mostrar.php?accion=vercompleto&i ....
Estrada EJ, et al. "Combined treatment of intrapancreatic autologous bone marrow nucleated cells and hyperbaric oxygen in Type 2 diabetes mellitus." *Cell Transplant.* 2008. 17: 1295-1304.
Laferrere B, et al. "Effect of weight loss by gastric bypass surgery versus hypocaloric diet on glucose and incretin levels in patients with type 2 diabetes." *J Clin Endocrinol Metab.* 2008. 93: 2479-2485. [online, retrieved on Aug. 10, 2012]. Retrieved from the internet URL: http://www.ncbi.nlm.nih.gov/pmc/articles/PMC2453054/?report=printable.
Hickey MS, et al. "A new paradigm for Type 2 diabetes mellitus: could it be a disease of the foregut?" *Ann Surg.* 1998.227: 637-644.
Weber M, et al. "Laparoscopic gastric bypass is superior to laparoscopic gastric banding for treatment of morbid obesity." *Ann Surg.* 2004. 240: 975-983.
Buchwald H, et al. "Weight and Type 2 diabetes after bariatric surgery: systemic review and meta-analysis." *Am J Med.* 2009. 122: 248-256.
Mithieux G, et al. "Portal sensing of intestinal gluconeogenesis is a mechanistic link in the diminution of food intake induced by diet protein." *Cell Metab.* 2005. 2: 321-329.
Troy S, et al. "Intestinal gluconeogenesis is a key factor for early metabolic changes after gastric bypass but not after gastric lap-band in mice." *Cell Metabolism.* 2008. 8: 201-211.

(Continued)

*Primary Examiner* — Taeyoon Kim
(74) *Attorney, Agent, or Firm* — Hamilton, Brook, Smith & Reynolds, P.C.

(57) ABSTRACT

The anatomic and functional arrangement of the gastrointestinal tract suggests an important function of this organ is its ability to regulate the trafficking of metabolites as well as control the equilibrium between tolerance and immunity through gut-associated lymphoid tissue, the neuroendocrine network, and the intestinal epithelial barrier. Combining nucleated cells from various tissues and introducing them directly into the small intestine will have a positive effect on diabetes.

24 Claims, 2 Drawing Sheets

(56) References Cited

OTHER PUBLICATIONS

Aguirre V, et al. "An endoluminal sleeve induces substantial weight loss and normalizes glucose homeostasis in rats with diet-induced obesity." *Obesity.* 2008. 16: 2585-2592.

Rodriguez-Grunert L, et al. "First human experience with endoscopically delivered and retrieved duodenal-jejunal bypass sleeve." *Surg Obes Relat Dis.* 2008. 4: 55-59.

Rubino F, et al. "The mechanism of diabetes control after gastrointestinal bypass surgery reveals a role of the proximal small intestine in the pathophysiology of Type 2 diabetes." *Ann Surg.* 2006. 266: 741-749.

Mithieux G, et al. "Induction of control genes in intestinal gluconeogenesis is sequential during fasting and maximal in diabetes." *Am J Physiol Endocrinol Metab.* 2004. 286: E370-E375.

Tobin V, et al. "Insulin internalizes GLUT-2 in enterocytes of healthy but not insulin-resistant mice." *Diabetes.* 2008. 57: 555-562.

Medina RA and Owen GI. "Glucose transporters: expression, regulation, and cancer." *Biol Res.* 2002. 35: 9-26. [online, retrieved on Aug. 10, 2012]. Retrieved from the internet URL: http://www.scielo.cl/scielo.php?script=sci_arttext&pid=S0716-97602002000100004&lng=es&nrm=iso&t . . . .

Ohtsubo K, et al. "Dietary and genetic control of GLUT-2 glycosylation promotes insulin secretion in suppressing diabetes." *Cell.* 2005. 123: 1307-1321.

Fujita S, et al. "Hypoglycemic detection at the portal vein is mediated by capsaicin-sensitive primary sensory neurons." *Am J Physiol Endodcrino Metab.* 2007. 293: E96-E101. [online, retrieved on Aug. 10, 2012]. Retrieved from the internet URL: http://ajpendo.physiology.org/content/293/1/E96.long.

Burcelin R, et al. Glucose sensing by the hepatoportal sensor is GLUT-2 dependent. Diabetes. 2000. 49: 1643-1648.

Schenk S, et al. "Insulin sensitivity: modulation by nutrients and inflammation." *J Clin Invest.* 2008. 118: 2992-3002.

Pories WJ. "Diabetes: the evolution of a new paradigm (ed.)." *Ann Surg.* 2004. 239: 12-13.

Kudo K, et al. "Transplantation of mesenchymal nucleated cells to prevent radiation-induced intestinal injury in mice." *J Radiation Res.* 2010. 51: 73-79.

Wu XH, et al. "Reversal of hyperglycemia in diabetic rats by portal vein transplantation of islet-like cells generated from bone marrow mesenchymal nucleated cells." *World J Gastroenterol.* 2007. 13: 3342-3349.

Darwish AA, et al. "Permanent access to the portal system for cellular transplantation using an implantable port device." *Liver Transplant.* 2004. 10: 1213-1215.

Massberg S, et al. "Platelets secrete stromal cell-derived factor 1 alpha and recruit bone marrow-derived progenitor cells to arterial thrombi in vivo." *J Exp Med.* 2006. 203: 1221-1233.

Stellos K, Gawaz M. "Platelet interaction with progenitor cells: potential implications for regenerative medicine." *Thromb Haemost.* 2007. 98: 922-929. (Prepublished online pp. 1-8.)

Hu, J., et al., "Long Term Effects of the Implantation of Wharton's Jelly-Derived Mesenchymal Stem Cells from the Umbilical Cord for Newly-Onset Type 1 Diabetes Mellitus," *The Japan Endocrine Society*, advance publication doi: 10.1507/ endocrj.EJ12-0343 (Nov. 16, 2012).

Kharaziha P, et al. "Improvement of liver function in liver cirrhosis patients after autologous mesenchymal stem cell injection: a phase I-II clinical trial." *Eur J Gastroenterol Hepatol.* 2009. 21: 1199-1205.

Bhansali A, et al. "Efficacy of autologous bone marrow derived stem cell transplantation in patients with Type 2 Diabetes Mellitus." *Nucleated cells Develop.* 2009. Ahead of Print.

Crisa L, et al. "Human cord blood progenitors sustain thymic T-cell development and a novel form of angiogenesis." Blood. 1999. 94: 3928-3940.

Ballantyne G, et al. "The surgical treatment of Type 2 diabetes mellitus: changes in HOMA insulin resistance in the first year following Laparoscopic Roux-en-Y Gastric Bypass (LRYGB) and Laparoscopic Adjustable Gastric Banding (LAGB)." *Obes Surg.* 2009.19: 1297-1303.

Alexandries TK, et al. "Resolution of diabetes mellitus and metabolic syndrome following Roux-en-Y gastric bypass and a variant of biliopancreatic diversion in patients with morbid obesity." *Obesity Surg.* 2007.17: 176-184.

Scopinaro N, et al. "A comparison of a personal series of biliopancreatic diversion and literature data on gastric bypass help to explain the mechanisms of resolution of Type 2 diabetes by the two operations." *Obesity Surg.* 2008. 18: 1035-1038.

Gersin KS, et al. "Duodenal-jejunal bypass sleeve: a totally endoscopic device for the treatment of morbid obesity." *Surg Innovation.* 2007. 14: 275-278.

Rodriguez L, et al. "Pilot clinical study of an endoscopic, removable duodenal-jejunal bypass liner for the treatment of type 2 diabetes." *Diabetes Technol Ther.* 2009. 11: 725-732.

LeRoux CW, et al. "Gut hormones as mediators of appetite and weight loss after Roux-en-Y gastric bypass.:" *Ann Surg.* 2007. 246: 780-785.

Dixon JB, et al. "Obesity and diabetes: the impact of bariatric surgery on Type 2 diabetes." *World J Surg.* 2009. 33: 2014-2021.

Mitheiux G, Andreeli F, Magnan C. "Intestinal gluconeogenesis: key signal of central control of energy and glucose homeostasis." *Curr Opin Clin Nutr Metab Care.* 2009. 12: 419-423.

Kellett GL, et al. "Sugar absorption in the intestine: the role of GLUT-2." *Ann Rev Nutr.* 2008. 28: 35-54.

Chandrasekharan B and Srinivasan S. "Diabetes and the enteric nervous system (review)." *Neurogastroenterol Motil.* 2007. 19: 951-960.

Hayashi Y, et al. "Topical transplantation of mesenchymal nucleated cells accelerates gastric ulcer healing in rats." *Am J Physiol Gastrointest Liver Physiol.* 2008. 294: 778-786.

Hayashi Y, et al. "Topical implantation of mesenchymal nucleated cells has beneficial effects on healing of experimental colitis in rats." *J Pharmacal Exp Ther.* 2008. 326: 523-531.

Nishida T, et al. "Cultured bone marrow cell local implantation accelerates ulcer healing in mice." *J Gastroenterol.* 2008.43: 124-135.

Tadauchi A, et al. "Novel cell-based therapeutic strategy for ischemic colitis with use of bone marrow-derived mononuclear cells in rats." *Dis Colon Rectum.* 2009. 52: 1443-1451.

Jiang H, et al. "Bone marrow mesenchymal nucleated cells reduce intestinal ischemia/reperfusion injuries in rats." *J Surg Res.* Aug. 22, 2009. (Epub ahead of print).

Kahaleh M, et al. "Factors predictive of malignancy and endoscopic resectability in ampullary neoplasia." *Am J Gastroenterol.* 2004. 99: 2335-2339.

Furst G, et al. "Portal vein embolization and autologous CD 133+ bone marrow nucleated cells for liver regeneration: initial experience." *Radiology.* 2007. 243: 171-179.

Juvenile Diabetes Cure Alliance, "State of the Cure" (2013).

\* cited by examiner

ADULT AND NEONATAL STEM CELL THERAPY TO TREAT DIABETES THROUGH THE REPAIR OF THE GASTROINTESTINAL TRACT

CROSS-REFERENCE TO RELATED APPLICATIONS

This application claims the benefit of provisional patent application Ser. No. 61/152,417 filed on Feb. 13, 2009. The entire teachings of the above application are incorporated herein by reference.

FEDERALLY SPONSORED RESEARCH

Not applicable

SEQUENCE LISTING OR PROGRAM

Not applicable

REFERENCES CITED

US Patent Documents

U.S. Pat. No. 6,808,702 December/2004 Pasricha et al
U.S. Pat. No. 5,175,103 December 1992 Lee et al.
U.S. Pat. No. 5,753,491 May 1998 Major et al.
U.S. Pat. No. 5,753,505 May 1998 Luskin
U.S. Pat. No. 5,851,832 December 1998 Weiss et al.
U.S. Pat. No. 5,869,463 February 1999 Major et al.
U.S. Pat. No. 5,968,829 October 1999 Carpenter
U.S. Pat. No. 5,980,885 November 1999 Weiss et al. U.S. Pat. No. 5,981,165 November 1999 Weiss et al.
U.S. Pat. No. 6,025,157 February 2000 Klein et al.
U.S. Pat. No. 6,497,872 December 2002 Weiss et al.

OTHER REFERENCES

Dixon. Obesity and diabetes: the impact of bariatric surgery in Type 2 diabetes. *World J Surg*. 2004. 20(6): 438-445.
Greenway S E, et al. Effects of obesity surgery on non insulin-dependent diabetes mellitus. *Arch Surg*. 2002. 137: 1109-1117.
Herman M A and Kahn B B. Glucose transport and sensing in the maintenance of glucose homeostasis and metabolic harmony. *J Clin Invest*. 2006. 116(7): 1767-1775.
Bhansali A, et al. Efficacy of autologous bone marrow derived stem cell transplantation in patients with Type 2 Diabetes Mellitus. *Nucleated cells Develop*. 2009. Ahead of Print.
Crisa L, et al. Human cord blood progenitors sustain thymic T-cell development and a novel form of angiogenesis. *Blood*. 1999. 94: 3928-3940.
Vina R, et al. Cell therapy: a new challenge for Type 2 Diabetes. Poster presentation at International Society of Cellular Therapy. May 2008.
Estrada E J, et al. Combined treatment of intrapancreatic autologous bone marrow nucleated cells and hyperbaric oxygen in Type 2 diabetes mellitus. *Cell Transplant*. 2008. 17: 1295-1304.
Laferrere B, et al. Effect of weight loss by gastric bypass surgery versus hypocaloric diet on glucose and incretin levels in patients with type 2 diabetes. *J Clin Endocrinol Metab*. 2008. 93: 2479-85
Hickey M S, et al. A new paradigm for Type 2 diabetes mellitus: could it be a disease of the foregut? *Ann Surg*. 1998. 227: 637-644.
Weber M, et al. Laparoscopic gastric bypass is superior to laparoscopic gastric banding for treatment of morbid obesity. *Ann Surg*. 2004. 240: 975-983.
Buchwald H, et al. Weight and Type 2 diabetes after bariatric surgery: systemic review and meta-analysis. *Am J Med*. 2009. 122: 248-256.
Ballantyne G, et al. The surgical treatment of Type 2 diabetes mellitus: changes in HOMA insulin resistance in the first year following Laparoscopic Roux-en-Y Gastric Bypass (LRYGB) and Laparoscopic Adjustable Gastric Banding (LAGB). *Obes Surg*. 2009. 19: 1297-1303.
Alexandries T K, et al. Resolution of diabetes mellitus and metabolic syndrome following Roux-en-Y gastric bypass and a variant of biliopancreatic diversion in patients with morbid obesity. *Obesity Surg*. 2007. 17: 176-184.
Scopinaro N, et al. A comparison of a personal series of biliopancreatic diversion and literature data on gastric bypass help to explain the mechanisms of resolution of Type 2 diabetes by the two operations. *Obesity Surg*. 2008. 18: 1035-1038.
Mithieux G, et al. Portal sensing of intestinal gluconeogenesis is a mechanistic link in the diminution of food intake induced by diet protein. *Cell Metab*. 2005. 2: 321-329.
Troy S, et al. Intestinal gluconeogenesis is a key factor for early metabolic changes after gastric bypass but not after gastric lap-band in mice. *Cell Metabolism*. 2008. 8: 201-11.
Aguirre V, et al. An endoluminal sleeve induces substantial weight loss and normalizes glucose homeostasis in rats with diet-induced obesity. *Obesity*. 2008. 16: 2585-92.
Gersin K S, et al. Duodenal-jejunal bypass sleeve: a totally endoscopic device for the treatment of morbid obesity. Surg Innovation. 2007. 14: 275-278.
Rodriguez-Grunert L, et al. First human experience with endoscopically delivered and retrieved duodenal-jejunal bypass sleeve. *Surg Obes Relat Dis*. 2008. 4: 55-59.
Rodriguez L, et al. Pilot clinical study of an endoscopic, removable duodenal-jejunal bypass liner for the treatment of type 2 diabetes. *Diabetes Technol Ther*. 2009. 11: 725-32.
LeRoux C W, et al. Gut hormones as mediators of appetite and weight loss after Roux-en-Y gastric bypass. *Ann Surg*. 2007. 246: 780-785.
Rubino F, et al. The mechanism of diabetes control after gastrointestinal bypass surgery reveals a role of the proximal small intestine in the pathophysiology of Type 2 diabetes. *Ann Surg*. 2006. 266: 741-749.
Mithieux G, et al. Induction of control genes in intestinal gluconeogenesis is sequential during fasting and maximal in diabetes. *Am J Physiol Endocrinol Metab*. 2004. 286: E370-E375.
Dixon J B, et al. Obesity and diabetes: the impact of bariatric surgery on Type 2 diabetes. *World J Surg*. 2009. 33: 2014-2021.
Tobin V, et al. Insulin internalizes GLUT-2 in enterocytes of healthy but not insulin-resistant mice. *Diabetes*. 2008. 57: 555-562.
Mitheiux G, Andreeli F, Magnan C. Intestinal gluconeogenesis: key signal of central control of energy and glucose homeostasis. *Curr Opin Clin Nutr Metab Care*. 2009. 12: 419-423.
Medina R A and Owen G I. Glucose transporters: expression, regulation, and cancer. *Biol Res*. 2002. 35: 9-26.
Ohtsubo K, et al. Dietary and genetic control of GLUT-2 glycosylation promotes insulin secretion in suppressing diabetes. *Cell*. 2005. 123: 1307-1321

Kellett G L, et al. Sugar absorption in the intestine: the role of GLUT-2. *Ann Rev Nutr*. 2008. 28: 35-54.

Fujita S, et al. Hypoglycemic detection at the portal vein is mediated by capsaicin-sensitive primary sensory neurons. *Am J Physiol Endodcrino Metab*. 2007. 293: E96-E101.

Burcelin R, et al. Glucose sensing by the hepatoportal sensor is GLUT-2 dependent. *Diabetes*. 2000. 49: 1643-1648.

Shenck S, et al. Insulin sensitivity: modulation by nutrients and inflammation. *J Clin Invest*. 2008. 118: 2992-3002.

Pories W J. Diabetes: the evolution of a new paradigm (ed.). *Ann Surg*. 2004. 239: 12-13.

Chandrasekharan B and Srinivasan S. Diabetes and the enteric nervous system (review). *Neurogastroenterol Motil*. 2007. 19: 951-960.

Hayashi Y, et al. Topical transplantation of mesenchymal nucleated cells accelerates gastric ulcer healing in rats. *Am J Physiol Gastrointest Liver Physiol*. 2008. 294: 778-786.

Hayashi Y, et al. Topical implantation of mesenchymal nucleated cells has beneficial effects on healing of experimental colitis in rats. *J Pharmacol Exp Ther*. 2008. 326: 523-531.

Nishida T, et al. Cultured bone marrow cell local implantation accelerates ulcer healing in mice. *J Gastroenterol*. 2008. 43: 124-135.

Tadauchi A, et al. Novel cell-based therapeutic strategy for ischemic colitis with use of bone marrow-derived mononuclear cells in rats. *Dis Colon Rectum*. 2009. 52: 1443-1451.

Jiang H, et al. Bone marrow mesenchymal nucleated cells reduce intestinal ischemia/reperfusion injuries in rats. *J Surg Res*. 2009. Aug. 22 (Epub ahead of print)

Kudo K, et al. Transplantation of mesenchymal nucleated cells to prevent radiation-induced intestinal injury in mice. *J Radiation Res*. 2009. October (Epub ahead of print)

Kahaleh M, et al. Factors predictive of malignancy and endoscopic resectability in ampullary neoplasia. *Am J Gastroenterol*. 2004. 99: 2335-2339.

Furst G, et al. Portal vein embolization and autologous CD 133+ bone marrow nucleated cells for liver regeneration: initial experience. Radiology. 2007. 243: 171-9.

Kharaziha P, et al. Improvement of liver function in liver cirrhosis patients after autologous mesenchymal stem cell injection: a phase I-II clinical trial. *Eur J Gastroenterol Hepatol*. 2009. 21: 1199-205.

Wu X H, et al. Reversal of hyperglycemia in diabetic rats by portal vein transplantation of islet-like cells generated from bone marrow mesenchymal nucleated cells. *World J Gastroenterol*. 2007. 13: 3342-9.

Darwish A A, et al. Permanent access to the portal system for cellular transplantation using an implantable port device. *Liver Transplant*. 2004. 10: 1213-1215.

Massberg S, et al. Platelets secrete stromal cell-derived factor 1 alpha and recruit bone marrow-derived progenitor cells to arterial thrombi in vivo. *J Exp Med*. 2006. 203: 1221-33.

Stellos K, Gawaz M. Platelet interaction with progenitor cells: potential implications for regenerative medicine. *Thromb Haemost*. 2007. 98: 922-29.

BACKGROUND OF THE INVENTION

1. Field of Invention

The invention relates to a method of treating diabetes. There are two types of diabetes, type 1 (T1D) and type 2 (T2D). About 10% of all Americans diagnosed with diabetes (more than 700,000) have T1D while the remaining other 90% of Americans that have diabetes, have type 2 diabetes. T2D (often referred to as adult onset diabetes) affects nearly 20 million people in the US. (CDC 2007) Diabetes, both T1D and T2D is the leading cause of blindness, renal failure and amputations, and patients have demonstrably shorter life spans. Increasingly diabetes is being understood as a metabolic disorder. This insight is leading to a new sort of pathology—the creation of inflammatory stress and an altered interaction between organ systems and between organ systems and the immune system resulting from the metabolism of certain substances. The evidence suggests that the organs themselves and the immune system are not impaired, but rather, they receive incorrect signals originating in the foregut due to the interaction of improper metabolites and the organ system. These signals then cause an improper cellular balance and function. While the dysfunction of the foregut in T1D and T2D is different, the original source of the incorrect signals leading to the pathology of the disease starts in the foregut.

2. Prior Art

T2D is a disease characterized by insulin insensitivity. Under normal circumstances, pancreatic islet cells release insulin in response to elevated levels of glucose in the bloodstream. Insulin drives glucose into peripheral tissues for use in building tissue and storing energy. However, in the setting of certain diets in susceptible individuals, glucose and insulin production is constantly switched on. As a protective mechanism, tissues subsequently become increasingly insensitive to insulin. Thus, T2D is a disease in which the environment (certain diets) damages the cellular niche of the foregut which triggers excess glucose production by the liver, which causes excess insulin production by the pancreas leading to insulin insensitivity in susceptible individuals.

T2D is caused by environmental insults due to the type of food consumed with the portion of the small intestine first exposed to food exiting the stomach most severely impacted. These environmental insults damage cellular niches in vulnerable individuals leading to the improper stimulation of the foregut during food digestion. Specifically, an imbalance of metabolites resulting from food digestion in the duodenum sends incorrect signals to the liver that over produces glucose that causes the pancreas to over produce insulin. Physiologic responses are eventually blunted as a protective mechanism in the face of constant signaling. Consequently, cells begin to look insulin resistant because there is too much glucose and insulin in the system. Overstressed pancreatic islets die because they cannot keep up with the required insulin production to overcome the excess amount of glucose being produced by the liver and the increasing insulin resistance of cells. In addition, some metabolites produced by the duodenum during food digestion need to communicate through nerve endings in the portal vein to signal hunger suppression to the brain. Advanced hyperglycemia damages these nerve endings exacerbating the problem. The following can be summarized as:

1) An improperly functioning duodenum that produces an imbalance of metabolites resulting in the excess production of glucose by the liver, insulin resistance, leading to a pancreatic burden that ends in islet necrosis; and 2) Improper hunger suppression due to damaged nerves primarily in the portal vein.

The combination of points 1 and 2 explains the high correlation between T2D and obesity.

Biliopancreatic diversion (BPD) and Roux-en-Y gastric bypass (RYGBP) effectively bypass the diseased portion of the intestinal tract so that the foregut (duodenum) is excluded and the distal small bowel becomes the new foregut. The distal small bowel is less impacted over time from the environmental insult that lead to the duodenum dysfunction because it is farther removed from the source of the insult which is certain partially undigested foods exiting the stomach. Consequently, immediately after the surgery, this undamaged portion of the small bowel becomes the new foregut, is attached to the stomach and remarkably, begins to produce proper metabolites in response to food intake. Thus, within days of surgery, blood sugar levels of patients return to a normal range and there is an increase in the release of certain hormones like GLP-1 that promote satiety. Interestingly, resolution of T2D following surgery is inversely proportional to duration of the disease; those who have had the disease for longer period of times prior to surgery experience lower rates of resolution. The longer a patient has lived with the disease, the greater the portion of the small bowel that is damaged, the greater the damage to islets of the pancreas, and the greater the damage to the nerve endings in the portal vein due to the prolonged impact of hyperglycemia.

With respect to type 1 diabetes (T1D), the goal of researchers is to 1) halt the progression of Type 1 diabetes (T1D) by re-introducing tolerance between the immune system and the pancreas and 2) regenerate the insulin producing capacity of the pancreas. Increasingly T1D is being understood as a metabolic disorder. This insight is leading to a new sort of pathology—the creation of inflammatory stress and an altered interaction between the organ systems and the immune system resulting from the metabolism of certain substances. The evidence suggests that the immune system is itself not impaired, but rather, it receives incorrect signals due to the interaction of improper metabolites and the organ system. These signals then cause an improper cellular balance and function.

We believe that the cause of type 1 diabetes originates in the small intestine. The primary functions of the gastrointestinal tract have traditionally been perceived to be limited to the digestion and absorption of nutrients and electrolytes, and to water homeostasis. A more attentive analysis of the anatomic and functional arrangement of the gastrointestinal tract, however, suggests that another extremely important function of this organ is its ability to regulate the trafficking of macromolecules between the environment and the host through a barrier mechanism. Together with the gut-associated lymphoid tissue and the neuroendocrine network, the intestinal epithelial barrier, with its intercellular tight junctions, controls the equilibrium between tolerance and immunity to nonself-antigens. When the finely tuned trafficking of macromolecules is deregulated due to certain environmental insults (most likely due to the ingestion of certain foods or pathogens) in genetically susceptible individuals, both intestinal and extra-intestinal autoimmune disorders can occur. Supporting this explanation are observations that diet modifies the incidence of diabetes and the phenotype of T-cells infiltrating the islets of Langerhans in animal models (NOD mice) of Type 1 diabetes. T-cells infiltrating the islets of Langerhans in Type 1 diabetics and in experimental models of autoimmune diabetes are intestinal in origin since they exhibit the b7-integrin receptor (gut associated homing receptor). Mesenteric lymphocytes from non-obese diabetic (NOD) mice can transfer diabetes to healthy recipients. We believe that concentrated nucleated cells injected into this environment can re-establishing proper intestinal function and arrest the autoimmune process by changing the interplay between altered epigenes and the environment.

We believe that the cause of type 1 diabetes originates in the small intestine. Specifically, T1D patients have an altered intestinal immune responsiveness. This altered mucosal immune system has been associated with the disease of T1D and is likely a major contributor to the failure to form tolerance, resulting in the autoimmunity that underlies type 1 diabetes. There are numerous cell types in the small intestine that play a role in proper immune system function, including the following:

Intraepithelial Lymphocytes.

Intraepithelial lymphocytes (IELs) are located at the basolateral side of the epithelial layer. Here they are exposed to a wide range of food and microbial antigens. One well-established function of IELs is their ability to protect the host from invasion by microorganisms that enter through the gastrointestinal tract. One subtype, the intestinal epithelial lymphocytes, are also at the mucosal interface and appear to play a key role in maintaining peripheral tolerance.

Intestinal Epithelial Cells.

Intestinal epithelial cells (IECs) comprise the lining epithelium of the primitive intestine with the role of transduction of inflammatory signals from luminal microbes via toll-like receptors and other signaling mechanisms. These cells serve as the permeability barrier between the external and internal milieus of the body.

M-Cells.

M-cells do not have well-developed microvilli and allow macromolecular transport, are specialized for delivering foreign antigens and microorganisms to organized lymphoid tissues within the mucosa of the small and large intestines.

Goblet Cells.

Goblet cells are specialized mucus-secretory cells found throughout the intestine. Intestinal mucus is a complex gel that covers the surface of the villous epithelium and contributes significantly to cytoprotection, offering many ecological advantages for the microbiota.

Paneth Cells.

Paneth cells represent one of the four major epithelial cell lineages in the small intestine and are the only lineage that migrates downward into the crypt base after originating in the crypt stem cell region. The location of Paneth cells adjacent to crypt nucleated cells suggests that they play a critical role in defending epithelial cell renewal. In response to pathogen attack, the Paneth cells secrete a wide spectrum of antimicrobial peptides against gram-negative and gram-positive bacteria, fungi, protozoa, and viruses.

The focus of research and therapy for T1D has been on pancreatic islet regeneration through various methods to include allogeneic islet transplantation, venous or arterial infusion of concentrated marrow nucleated cells into the area of the pancreas, non myeloablative immune conditioning followed by a systematic autologous or allogeneic stem cell transplantation and immune suppression drugs. Unfortunately, there is no cure for T1D and patients diagnosed with this disease require exogenous insulin injections to live.

The focus of research and therapy for T2D has been on drugs to improve insulin sensitivity, weight loss through surgery or diet, and more recently, a Teflon sleeve that covers the duodenum. This sleeve allows the passage of food from the stomach to the distal portion of the small intestine without having the food contact the duodenum.

All of the major functions of the body are related. The source of diabetes is the foregut and when this organ is impaired, it results in incorrect protein signals being produced that cause problems in other organs. In the case of T1D, the incorrect signals cause the immune system to attack cells that make insulin. In the case of T2D, the incorrect signals cause the liver to overproduce glucose which then makes the pancreas have to over produce insulin and results in insulin insensitivity in peripheral tissues. The focus of prior art for both T1D and T2D has been on organs and tissues which are damaged as a result of diabetes, with the primary focus being the pancreas. We believe in the case of both disease states, the focus needs to be on the organ (ie the gastrointestinal tract) the disease emanates from, and not the organs downstream (ie pancreas and other peripheral tissues) that are damaged as a result of the malfunctioning gastrointestinal tract.

U.S. Pat. No. 6,808,702 provides a method of implantation of stem cells into a gastrointestinal organ for purposes of repopulating various cellular components and/or providing a source of biological material for therapeutic intent. The source of these stem cells can be embryonic or adult neural and non-neural tissue, (e.g. bone marrow or fat tissue) U.S. Pat. No. 6,808,702 goes on to define a gastrointestinal organs to include hollow and solid organs. Hollow gastrointestinal organs include those that make up the alimentary tract, such as the mouth, esophagus, stomach, and bowels. Solid gastrointestinal organs include those that drain into the gastrointestinal alimentary tract such as the liver, gall bladder and pancreas. With respect to diabetes, U.S. Pat. No. 6,808,702 teaches that it is a disease of a solid organ as defined by the patent as a gastrointestinal organ and not a hollow organ as defined by the patent. Specifically, U.S. Pat. No. 6,808,702 teaches a method of producing enhanced levels of insulin in a patient by implanting stem cells and/or progeny thereof into the pancreas, which is considered a gastrointestinal organ as defined by the patent because it is a solid organ that drains into the gastrointestinal alimentary tract. For example U.S. Pat. No. 6,808,702 states "Further, this invention can also be used to provide therapy for disorders that are not traditionally considered gastrointestinal disorders but are related to organs that are considered gastrointestinal organs (e.g. liver, gall bladder, and pancreas) in that the organs drain into the gastrointestinal alimentary canal. Such disorders include diabetes, which can be treated by means of implantation of stem cells into the pancreas of a patient to cause enhancement of insulin production." It is important to note that U.S. Pat. No. 6,808,702 broadly defines gastrointestinal organs to include the pancreas; goes on to define diabetes as not being thought of as a gastrointestinal disorder; and instructs that stem cells be injected into the pancreas (a solid organ) as a possible therapy for diabetes. It is important to note that U.S. Pat. No. 6,808,702 states that diabetes is not traditionally thought of as a gastrointestinal disorder and specifically teaches away from the art disclosed here by instructing the injection of stem cells into the solid organ pancreas.

The art disclosed here is patently different from what is disclosed in U.S. Pat. No. 6,808,702. This art narrowly defines gastrointestinal tract to include hollow organs that make up the alimentary tract to include the stomach and bowels but does not include any solid organs. Opposed to the traditional view that diabetes is not a gastrointestinal disorder as taught by U.S. Pat. No. 6,808,702; the art disclosed herein specifically identifies diabetes as a disease that originates in the hollow organs of the gastrointestinal tract and not of the solid organ pancreas. This art then goes on to specifically teach that an effective therapy for diabetes is to implant nucleated cells from various tissues into the hollow organs of the gastrointestinal tract, specifically the duodenum. Conversely, U.S. Pat. No. 6,808,702 broadly defines gastrointestinal organs to include the pancreas, defines diabetes as being a disease of the solid organ pancreas, and in the art teaches to inject into the solid organ of the pancreas.

Some of the prior art referred to above use treating compositions that contain nucleated cells to include nucleated cells from bone marrow aspirates, fat aspirates, or mobilized peripheral blood. Specifically, the prior art teaches the delivery of the cells into the venous or arterial system. However, none of the prior art is delivering the nucleated cells directly into the appropriate tissue. This art teaches a method of injecting the treating composition directly into the tissue of gastrointestinal tract with a focus on the foregut. In view of the above, the present invention seeks to improve clinical outcomes by delivering a treating composition into the foregut which is the source of the disease. Compositions that contain nucleated cells are an obvious choice to include in the composition because nucleated cells have the demonstrated ability to regulate the cellular activity of surrounding cells and to repair the function of damaged tissue and immune systems. Tissues whose nucleated cell population are rich in cells that contain sub populations that are often referred to as stem cells include bone marrow aspirate, fat aspirate, cord blood, mobilized peripheral blood, Wharton's jelly, and other after birth tissue. Since diabetes ultimately damages other organ systems, it is reasonable to combine the treatment of the foregut with a method of treating other tissue affected by the disease. Thus combining a method of delivering cells into the foregut with a systemic delivery of nucleated cells into the venous or arterial system is appropriate.

SUMMARY OF THE INVENTION

Diabetes can be reversed through the repair the duodenum by implanting concentrated nucleated cells that include nucleated cells from various sources directly into the wall of the duodenum through an endoscopic procedure. The implantation can be carried out via local injection, as for example into a wall of the duodenum. This therapy can be augmented by combining direct injection into the gastrointestinal tract of the treating composition with arterial or venous delivery. Several different tissue sources rich in nucleated cell populations that contain nucleated cells can be used alone or in combination in preparing the treating composition.

DETAILED DESCRIPTION OF THE INVENTION

T2D can be reversed through the repair of the duodenum by injecting concentrated nucleated cells from various sources directly into the wall of the duodenum through an endoscopic procedure. This procedure can be combined with introducing a portion of the treating composition into the portal vein and or duodenal artery through a catheter based procedure. This procedure should 1) reset/repair the proper function of digestion and metabolite production in the duodenum and 2) repair of the nerve endings of the portal vein. The result will be an improvement in establishing normal glucose levels, support for the regeneration of the insulin producing capacity of the pancreas, improvement in insulin resistance, and the re-establishment of hunger suppression signals in response to food intake. Consequently, the therapy should be effective for both T2D and the co-morbidity of obesity associated with T2D.

The progression of T1D can be halted prior to the destruction of the pancreas by re-setting of the immune system. This can be accomplished through the repair of the small intestine by injecting a treating composition of nucleated cells into the wall of the duodenum through an endoscopic procedure to reset/repair the interaction between the immune system and the insulin producing islets of the pancreas.

DRAWINGS

Figures

DETAILED DESCRIPTION

Figure 1:
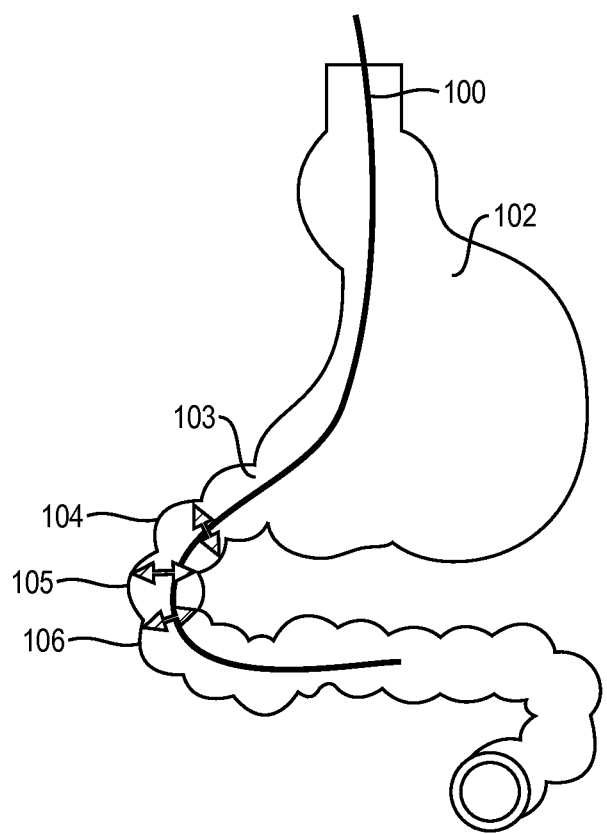
FIG. 1 is a perspective view for explaining one embodiment of the present invention.

First Embodiment—FIG. 1

In the interest of clarity, numerous different surgical protocols and surgical devices currently available can be used to implant a treating composition into the wall of the gastrointestinal tract. Also, numerous different methodologies can be used for concentrating nucleated cells from the various tissues mentioned above in order to create the treating composition. The source of the cells can be the patient themselves or from other donors. Some of these tissues can be sourced, concentrated and delivered at point of care. Other sources of cells can be sourced, processed in a laboratory, and then delivered to the patient. It will, of course, be appreciated that in the development of any surgical protocol designed to implement the art described, numerous implementation-specific decisions must be made in order to fit a particular patient's profile and that these specific protocols will vary from one surgeon and patient to another. Moreover, it will be appreciated that such a development effort might be complex and time-consuming, but would nevertheless be a routine undertaking for those of ordinary skill in the art having the benefit of this disclosure. For example, different injection patterns, needle gauges, and combinations of nucleated cells from various sources can be used to create and deliver the treating composition. The treating composition can be delivered through and endoscopic procedure or during an open procedure. In addition to cells, other types of treating compositions could be delivered in combination or individually as part of the treating composition that contain for example, platelets, growth factors or other proteins or therapeutic agents to include pharmaceuticals.

FIG. 1 is a perspective view of the stomach (102) which is connected to the foregut. (103) Several different endoscopic surgical tools exist to access the gastrointestinal tract and to inject cells into the wall of the duodenum. (100) Such tools are flexible in nature and are designed to move easily through the curved space within the gastrointestinal tract. These same tools can be used to implant a treating composition directly into the walls of the tissue comprising the gastrointestinal tract. Such direction injections can move in a spiral pattern along the walls of the tissue. (104, 105, 106)

Figure 2:
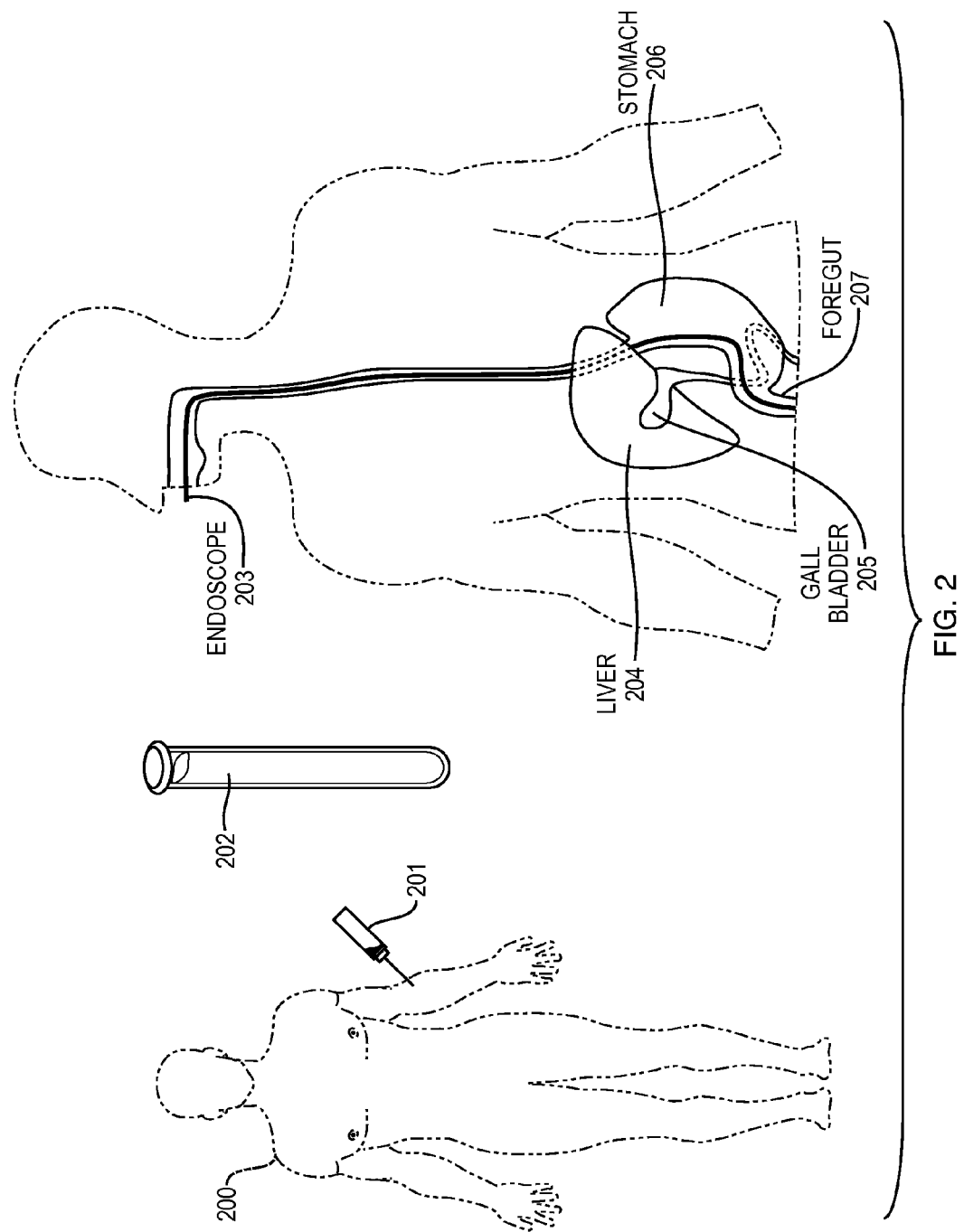
FIG. 2 is a perspective view for explaining an embodiment of the present invention whereby the cells are sourced from the patient being treated.

FIG. 2 is a perspective of a surgical protocol of treating a patient (200) with tissue rich in stem cells sourced from their own body. (201) This tissue is then processed to concentrate the nucleated cells including the stem cells. (202) Such methods of concentration can be done point of care during same procedure as the sourcing of the cells and the delivery of the cells to the gastrointestinal tract. The treating composition is then delivered through and endoscopic tool (203) to the hollow organs of the gastrointestinal tract that include the stomach (206) and foregut (207.) Other organs such as the liver (204) and gallbladder (205) and pancreas (not shown) can also be treated by infusing a portion of the treating composition into the venous or arterial system.

In accordance with the present invention, the method of sourcing, concentrating, and delivering directly a treating composition rich in nucleated cells to include stem cells into the tissue of the foregut may be implemented using various types of laboratory and or surgical equipment. Thus the scope of the invention should be determined by the appended claims and their legal equivalents, and not by the examples given.

It will be appreciated that numerous different methods exist to concentrate the nucleated cells from various tissue to include bone marrow aspirate and fat aspirate. These methods can employ off site laboratory methods or devices designed to be used at the patients side (ie point of care) For example, their exists several centrifugation based protocols such as a ficoll separation method, cell washing technology, and apheresis technology for removing a large portion of the non-nucleated red blood cells and plasma from marrow aspirate and or cord blood. Such methods are well known in the art. For removing the extracellular matrix material from fat, whartons jelly, and other solid tissues, several well known protocols such as enzymatic digestion with collagenase are well known in the art. With all of these protocols, some material such as plasma and red cells remain in the concentrate.

DEFINITIONS

Gastrointestinal tract means hollow organs and include the alimentary tract to include the stomach and bowels.

T1D means type 1 diabetes.

T2D means type 2 diabetes.

Nucleated cell means a cell that contains a nucleus.

The invention claimed is:

1. A method to treat diabetes comprising:
implanting concentrated nucleated cells including stem cells from multiple source tissues directly into tissue of the duodenum to reset or repair the immune system or to reset or repair metabolite production in the duodenum, the concentrated nucleated cells being a heterogeneous population of cells and including cells from a bone marrow aspirate, a fat aspirate, cord blood, Wharton's Jelly, or afterbirth tissue.

2. The method according to claim 1 wherein the concentrated nucleated cells are implanted through an endoscopic procedure.

3. The method according to claim 1 wherein the concentrated nucleated cells are injected into the wall of the duodenum.

4. The method according to claim 1 wherein the concentrated nucleated cells include cells from a bone marrow aspirate.

5. The method according to claim 1 wherein the concentrated nucleated cells include cells from a fat aspirate.

6. The method according to claim 1 wherein the concentrated nucleated cells include cells from cord blood.

7. The method according to claim 1 wherein the concentrated nucleated cells include cells from Wharton's Jelly.

8. The method according to claim 1 wherein the concentrated nucleated cells are derived from autologous tissue.

9. The method according to claim 1 wherein the concentrated nucleated cells have been concentrated from source tissue by removing material that does not contain nucleated cells.

10. The method according to claim 1 further comprising delivering a portion of the concentrated nucleated cells into the venous or arterial system.

11. The method according to claim 1 further comprising:
sourcing nucleated cells from a patient; and
preparing the concentrated nucleated cells using the nucleated cells sourced from the patient, wherein the sourcing, preparing and implanting are performed in one point-of-care procedure.

12. The method according to claim 1 wherein the concentrated nucleated cells are implanted into the tissue of the duodenum of a patient diagnosed with type-1 diabetes during the progression of the destruction of the islets of the patient's pancreas.

13. The method according to claim 1 wherein the concentrated nucleated cells include subpopulations of nucleated cells from respective source tissues.

14. The method according to claim 1 further comprising:
in one point-of-care procedure,
preparing a combination of concentrated nucleated cells from multiple source tissues, the nucleated cells being derived from autologous tissue; and
implanting the combination directly into tissue of the duodenum of a patient diagnosed with type-1 diabetes during the progression of the destruction of the islets of the patient's pancreas.

15. A method to treat diabetes comprising:
obtaining tissue from a tissue source, the tissue source being bone marrow aspirate, cord blood, adipose tissue, Wharton's Jelly, or afterbirth tissue;
preparing concentrated nucleated cells including stem cells by removing a substantial amount of material other than nucleated cells from the tissue obtained, the concentrated nucleated cells being a heterogeneous population of cells; and
implanting the concentrated nucleated cells directly into tissue of the duodenum to reset or repair the immune system or to reset or repair metabolite production in the duodenum.

16. The method according to claim 15 wherein the concentrated nucleated cells include subpopulations of nucleated cells from the tissue source.

17. The method according to claim 15 performed in one point-of-care procedure,
wherein the tissue source is bone marrow aspirate from a patient,
wherein preparing the concentrated nucleated cells includes removing a large portion of non-nucleated red-blood cells and plasma from the bone marrow aspirate, and
wherein implanting the concentrated nucleated cells includes injecting the concentrated nucleated cells directly into the wall of the duodenum of the patient using an endoscope.

18. The method according to claim 17 wherein preparing the concentrated nucleated cells includes combining the concentrated nucleated cells from the bone marrow aspirate with nucleated cells sourced from placental tissue of a donor other than the patient.

19. The method according to claim 15 wherein the concentrated nucleated cells are injected into the wall of the duodenum of a patient diagnosed with type-1 diabetes during the progression of the destruction of the islets of the patient's pancreas.

20. The method according to claim 15 wherein the concentrated nucleated cells are implanted to reset or repair the interaction between the immune system and the insulin producing islets of the pancreas through repair of the duodenum.

21. The method according to claim 1 wherein the concentrated nucleated cells are implanted to reset or repair the interaction between the immune system and the insulin producing islets of the pancreas through repair of the duodenum.

22. A method to treat a patient diagnosed with type-1 diabetes, the method comprising:
preparing concentrated nucleated cells including stem cells from source tissue by removing material that does not contain nucleated cells from the source tissue and leaving a heterogeneous population of cells, the source tissue including a bone marrow aspirate from the patient, a fat aspirate from the patient, cord blood, or afterbirth tissue; and
implanting the concentrated nucleated cells into tissue of the patient's duodenum during the progression of the destruction of the islets of the patient's pancreas to reset or repair the patient's immune system.

23. The method according to claim 22 wherein preparing the concentrated nucleated cells includes combining the concentrated nucleated cells from multiple source tissues.

24. The method according to claim 22 wherein the concentrated nucleated cells are implanted to reset or repair the interaction between the immune system and the insulin producing islets of the pancreas through repair of the duodenum.

* * * * *